United States Patent [19]

Mori et al.

[11] 4,387,218
[45] Jun. 7, 1983

[54] ANTHRACYCLINE ANTIBIOTICS FA-1180 B AND B₁, OR SALTS THEREOF

[75] Inventors: Hiroyuki Mori; Yasuo Ogawa; Hideo Sugi; Noboru Fujikawa, all of Moriyama; Kiyoshi Tamai, Hikone, all of Japan

[73] Assignee: Ishihara Sangyo Kaisha, Ltd., Osaka, Japan

[21] Appl. No.: 299,259

[22] Filed: Sep. 3, 1981

Related U.S. Application Data

[63] Continuation of Ser. No. 187,031, Sep. 15, 1980, abandoned.

[30] Foreign Application Priority Data

Sep. 14, 1979 [JP] Japan .................. 54-118044

[51] Int. Cl.³ .............................................. C07H 15/24
[52] U.S. Cl. ...................................... 536/6.4; 424/180
[58] Field of Search .............................. 536/17 A, 6.4

[56] References Cited

U.S. PATENT DOCUMENTS 4,147,778  4/1979  Umezawa et al. ................. 536/17 A
4,303,785  12/1981 Umezawa et al. ................. 536/17 A

FOREIGN PATENT DOCUMENTS 1426637  3/1976  United Kingdom .

OTHER PUBLICATIONS

Brazhnikova et al., "The Journal of Antibiotics", vol. XXVII, No. 4, Apr. 1974, pp. 254-259.
Zbarskiy et al., "Antibiotiki", vol. 25, 1980, pp. 488-492.

Primary Examiner—Johnnie R. Brown
Attorney, Agent, or Firm—Sughrue, Mion, Zinn, Macpeak & Seas

[57] ABSTRACT

An anthracycline antibiotic FA-1180 A, A₁, B or B₁, or salts thereof, said antibiotic having the formula (I):

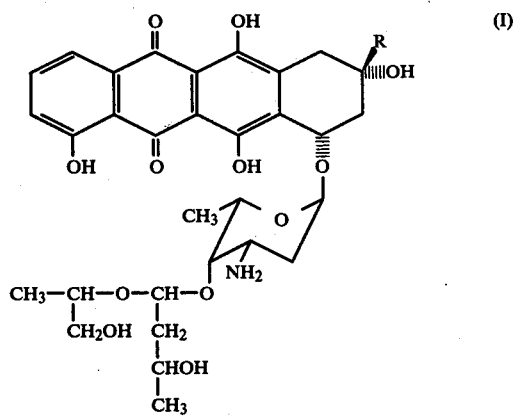

wherein R represents an acetyl group or a 1-hydroxyethyl group.

1 Claim, 15 Drawing Figures

ANTHRACYCLINE ANTIBIOTICS FA-1180 B AND B₁, OR SALTS THEREOF

This is a continuation of application Ser. No. 187,031, filed Sept. 15, 1980, now abandoned.

BACKGROUND OF THE INVENTION

This invention relates to novel anthracycline antibiotics FA-1180 A, $A_1$, B and $B_1$, or salts thereof.

DETAILED DESCRIPTION OF THE INVENTION

The present inventors have found that the new strain of actinomycetes, FA-1180 strain isolated from the soil collected on the shore of Lake Biwa, Shiga, Japan, has the ability to produce a novel antibiotic FA-1180 A, $A_1$, B or $B_1$ (hereunder referred to as antibiotic A, $A_1$, B or $B_1$). The antibiotic has strong ability to inhibit the growth of Gram-positive microorganisms, and it also has antitumor activity. Therefore, it is useful as an active ingredient of a medicine such as a disinfectant for medical devices or chemotherapeutics to treat bacteriasis in human beings or animals.

The antibiotic of this invention can be produced, for example, by extracting, separating and purifying from the culture broth of the strain FA-1180. The strain used in such fermentation is a novel actinomycetes that was isolated from the soil on the shore of Lake Biwa, designated *Actinomadura roseoviolacea* var. biwakoensis nov. var. (hereunder referred to as the Strain) and deposited in the Fermentation Research Institute, Agency of Industrial Science and Technology, Japan, as FERM-P 5155, and its mycological properties are as follows.

(1) Morphological properties:

For observation of its morphological properties, the Strain was cultivated on seven media, yeast extract-malt extract agar medium (ISP No. 2), oatmeal agar medium (ISP No. 3), ISP No. 3 medium containing B vitamins (ISP No. 3V), inorganic salts-starch agar medium (ISP No. 4), ISP No. 4 medium containing B vitamins (ISP No. 4V), glycerol-asparagine agar medium (ISP No. 5), and ISP No. 5 medium containing B vitamins (ISP No. 5V).

Figure 1:
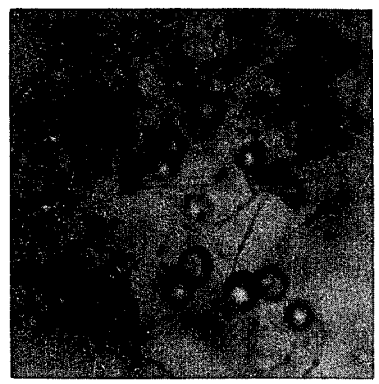
FIGS. 1 and 2 are each an optical micrograph of the spore chains of strain FA-1180.
Figure 2:
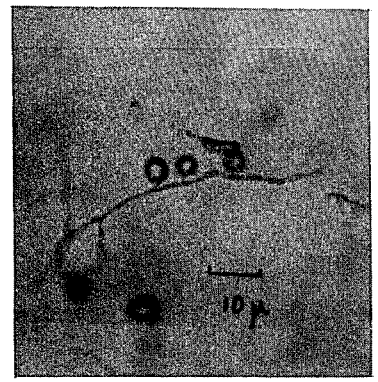
Figure 3:
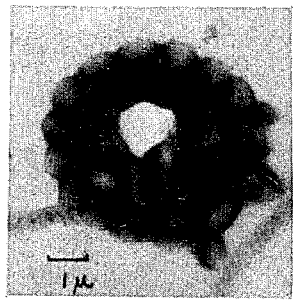
FIGS. 3, 4 and 5 are each an electron micrograph of the spore chains of strain FA-1180.
Figure 4:
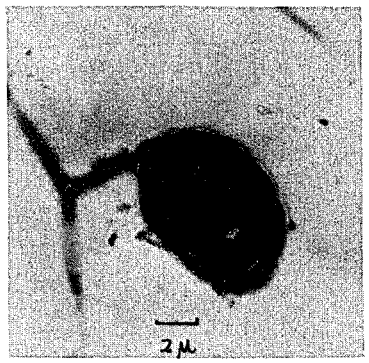
Figure 5:
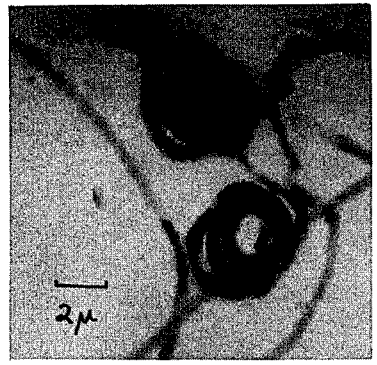
Figure 6:
FIG. 6 is another electron micrograph of the spore chains of strain FA-1180.

No fragmentation or separation of substrate mycelium was observed in either medium. Aerial mycelium was not observed in ISP No. 4 or ISP No. 5, slightly observed in ISP No. 5V, and a long straight or flexible aerial mycelium was observed in ISP No. 2, ISP No. 3, ISP No. 3V and ISP No. 4V. Spore chains were formed on the tips of very short aerial mycelia which were, generally, monopodially branched from the long aerial mycelium, and they looked like globular sporangia (3 to $8\mu$ in size) under an optical microscope (see FIGS. 1 and 2 which are each an optical micrograph of the spore chains of strain FA-1180). Such morphological features were observed in ISP No. 3, ISP No. 3V and ISP No. 4V, but little in ISP No. 2 and ISP No. 5V. Direct observation with an electron microscope or indirect observation by carbon replication revealed that the spore chains formed a spiral wound closely two to five turns into a doughnut (FIGS. 3, 4 and 5 which are each an electron micrograph of the spore chains of strain FA-1180), but spore chains that resembled a pseudosporangium were also found (FIG. 6 which is another electron micrograph of the spore chains of strain FA-1180). The spores were oval, $0.8 \sim 1.1 \times 0.6 \sim 1.0\mu$ in size and had a smooth surface.

ISP No. 3V, ISP No. 4V and ISP No. 5V were prepared by adding the following B vitamins to one liter of ISP No. 3, ISP No. 4 and ISP No. 5: 0.5 mg of thiamine hydrochloride, 0.5 mg of riboflavin, 0.5 mg of niacin, 0.5 mg of pyridoxine hydrochloride, 0.5 mg of inositol, 0.5 mg of calcium pantothenate, 0.5 mg of p-aminobenzoic acid and 0.25 mg of biotin.

(2) Cultural characteristics of *Actinomadura roseoviolacea* var. biwakoensis nov. var. on various media.

TABLE 1

Cultural Characteristics of *Actinomadura roseoviolacea* var. *biwakoensis* nov. var. on Various Media

| | Medium and Abbreviation Thereof | Growth | Aerial Mycelium | Soluble Pigment |
|---|---|---|---|---|
| A | Trypton-yeast extract broth (ISP No. 1) | Fair, Pale yellowish flaky growth on bottom of tube, Partially light orange~strong reddish orange ring on surface, in contact with glass | Restricted, White~pale pink | Slightly, Bright reddish orange |
| B | Yeast extract-malt extract agar (ISP No. 2) | Good, Remarkably raised, Many folds, Strong orange~deep reddish orange, turning later into deep red | Fair, Pink~purplish pink | Slightly, Strong reddish orange |
| C | Oatmeal agar (ISP No. 3) and ISP No. 3V | Fair~somewhat restricted, Flat, Spreading, Strong | Fair, Powdery, Some drops of color- | Strong reddish orange |

TABLE 1-continued
Cultural Characteristics of *Actinomadura roseoviolacea* var. *biwakoensis* nov. var. on Various Media

| Medium and Abbreviation Thereof | Growth | Aerial Mycelium | Soluble Pigment |
|---|---|---|---|
| | reddish orange | less guttation, White~pale pink | |
| D  Inorganic salts-starch agar (ISP No. 4) | Restricted, Penetrating into medium, Light yellowish brown | Scant, White | None |
| E  ISP No. 4V | Good, Somewhat raised, Strong reddish orange | Fair~good, Pale pink | Strong orange zone around growth |
| F  Glycerol-asparagine agar (ISP No. 5) | Very poor, Light yellowish brown | None | None |
| G  ISP No. 5V | Good, Remarkably raised, Strong reddish orange~deep reddish orange | Restricted, White~pale pink | Slightly, Bright orange |
| H  Peptone-yeast extract-iron agar (ISP No. 6) | Moderate, Raised, Many fine folds, Grayish brown~dark grayish brown | None | Slightly, Deep red |
| I  Tyrosine agar (ISP No. 7) | Fair~somewhat restricted, Flat, Dull red, turning later into deep red purple | None | None |
| J  ISP No. 7V | Fair, Flat, Deep red purple | None | Deep red purple |
| K  Sucrose nitrate agar (Waksman No. 1) | Fair, Light orange~strong reddish orange pink | Restricted, White~pale Reddish orange | None or slightly, |
| L  Waksman No. 1V | Fair~good, Bright orange~deep red purple | Fair, Pale pink~pale yellowish pink | Deep red purple |
| M  Glucose-asparagine agar (Waksman No. 2) | Poor, Pale yellow | None | None |
| N  Waksman No. 2V | Fair~good, Somewhat raised, Bright reddish orange | Scant, White~pale pink | Bright orange |
| O  Bouillon agar (Waksman No. 8) | Fair, Dull red~grayish red | Very scant, White | Dull red |
| P  Glucose-bouillon agar | Very good, Remarkably raised, Many folds, Dull red~dark red | Very scant, White | Dull red |
| Q  Potato scab (Waksman No. 40) | Fair, Somewhat raised, Strong reddish orange~dull purplish red | Restricted, White~grayish pink | Grayish pink~grayish red |
| R  Löffler's blood serum | Fair~somewhat restricted, Bright yellowish red, turning later into deep red purple | None | Slightly, Deep red purple |
| S  Skim milk (Waksman No. 41) | Fair~somewhat restricted, Ring, Bright orange~bright reddish orange | None | Slightly, Light orange~bright orange |
| T  Calcium malate agar | Very poor or no growth | None | None |
| U  Calcium malate agar V | Somwhat restricted, Flat, Spreading, Vivid red purple | None | Vivid red purple |
| V  Glycerol-calcium malate agar (Waksman No. 7) | Restricted~poor, Bright orange | None | None |
| W  Waksman No. 7V | Fair, Dull red | None | None or slightly dull red |
| X  Bouillon-gelatin stab (20° C.) | No growth | | |

The media identified by V in the column of "Media and their abbr." of Table 1 were prepared in the same manner as in the preparation of the media containing B vitamins, described before.

The respective tests were conducted in accordance with the methods described in *International Journal of Systematic Bacteriology*, Vol. 16, p. 313, in 1966 and S. A. Waksman, *The Actinomycetes*, Vol. 2. Unless otherwise noted, all media were held at 27° to 28° C. for 21 days for incubation of the Strain, and color observation was made in compliance with *Manual of Color Names*, published by Nippon Shikisai Kenkyu-jo in 1973.

After the 21-day incubation on ISP No. 2, ISP No. 3, ISP No. 3V, ISP No. 4, ISP No. 4V, ISP No. 5 and ISP No. 5V, the Strain was treated with 0.05 N hydrochloric acid and 0.05 N sodium hydroxide, and the results indicated in Table 2 below were obtained.

TABLE 2

Change in Growth and Soluble Pigment with pH

| Media (abbr.) | Growth or Soluble Pigment | 0.05N Hydrochloric Acid Treatment | No Treatment | 0.05N Sodium Hydroxide Treatment |
|---|---|---|---|---|
| 1 ISP No. 2 | Growth | Dull red | Dark red | Deep purplish red |
| | Soluble pigment | Dull yellowish orange | Dull orange | Dull red purple |
| 2 ISP No. 3 and ISP No. 3V | Growth | No change (bright orange) | Bright orange | Light grayish purple |
| | Soluble pigment | Bright reddish orange | Bright orange | Bright purple~light grayish purple |
| 3 ISP No. 4V | Growth | No change (vivid reddish orange) | Vivid reddish orange | Bright purple |
| 4 ISP No. 5V | Growth | No change (bright orange) | Bright orange | Bright purple |

(3) Physiological characteristics (a) Growth temperature range (tested on a yeast extract-malt extract broth every five degrees in the range of from 15° to 50° C.): Grew up to 40° C.

Optimum temperature range: 35° to 40° C.

(b) Liquefaction of gelatin: negative (c) Peptonization of skim milk: positive (weak and slow)

Coagulation of skim milk: positive (weak and slow)

(d) Liquefaction of Löffler's blood serum: negative (e) Production of melanoid pigment:
  Trypton-yeast extract broth: negative
  Tyrosine agar medium: negative
  Peptone-yeast extract-iron agar medium: negative (f) $H_2S$ formation: negative (g) $NH_3$ formation: negative (h) Nitrate reduction: positive (strong)

(i) Starch hydrolysis: positive (weak)

(4) Utilization of carbon sources (tested on ISP No. 9 medium)

TABLE 3

Utilization of Various Carbon Sources

| Growth | Carbon Sources |
|---|---|
| Positive (good or fair growth) | D-Glucose, L-Arabinose, D-Galactose, D-Fructose, Salicin, Sucrose, L-Rhamnose, Inositol, D-Xylose, D-Mannose, D-Mannitol, Maltose, D-Lactose, Trehalose, Cellobiose, Melibiose |
| Doubtful | D-Sorbitol |
| No | Inulin, Raffinose |

(Addition of B vitamins promoted the growth.)

(5) Cell wall composition

The Strain was cultured in a trypton-yeast extract agar medium (ISP No. 1) and a purified wall was prepared in accordance with the method of T. Yamaguchi described in *J. Bacteriol.*, Vol. 89, pp. 444–453, 1965, and subjected to an analysis. The wall was subjected to amino acid analysis by a Yanagiomoto High-Speed Amino Acid Analyzer. Stereoisomers of α,ε-diaminopimelic acid were determined by the method of Hoare et al., described in *Biochem. J.*, Vol. 65, pp. 441–447, 1957. Sugar determination was made by a GLC mass spectral analysis (Shimadzu LKB-9000) after trimethyl-silylation. The Strain had in the cell wall meso-diaminopimelic acid as a characteristic amino acid and madurose as sugars, but it did not contain arabinose, galactose or xylose.

In summary, the Strain belongs to Sugar pattern B of Cell wall type III described on page 658 of *Bergey's Mannual of Determinative Bacteriology*, 8th Ed., since it contains meso-diaminopimelic acid and madurose in the cell wall. The spore chains form a spiral wound closely into a doughnut, or they resemble sporangia. The color of growth is orange~red~purple, the aerial mycelium is white~pink, and the soluble pigment is orange~-red—purple, and they change with pH. The growth was found to be promoted by B vitamins.

These characteristics all suggest that the Strain is a microorganism of the genus Actinomadura. Nonomura et al. identifies new five strains that belong to the genus Actinomadura (*J. Ferment. Technol.*, Vol. 49 (11), 1971, pp. 904–912) and *Actinomadura roseoviolacea* is fairly close to the Strain. We therefore compared the Strain with *Actinomadura roseoviolacea* KCC.A-0145. The results are shown in Table 4. In spite of several differences (e.g., growth on various media and utilization of carbon sources), the two strains are similar to each other in respect of their basic characteristics. Therefore, we identified the Strain to be a new variant of *Actinomadura roseoviolacea* and designated it *Actinomadura roseoviolacea* var. biwakoensis nov. var. Actinomycetes easily undergo either artificial or natural mutation to form mutant strains, and these strains are included within *Actinomadura roseoviolacea* var. biwakoensis nov. var. as defined in this invention.

TABLE 4

| Medium | Examination Item | Actinomadura roseoviolacea var. biwakoensis nov. var. | Actinomadura roseoviolacea KCC A-0145 |
|---|---|---|---|
| ISP No. 1 | Growth | Ring, Light orange~strong reddish orange | Flaky growth on bottom of tube, Pale yellow |
| | Soluble pigment | Slightly, Bright reddish orange | None |
| ISP No. 4 | Growth | Restricted, Penetrating into medium, Light yellowish brown | Restricted, Spreading, Light reddish brown |
| | Aerial mycelium | Scant, White | Moderate, White~pale pink |
| ISP No. 5V | Aerial mycelium | Restricted, White~pale pink | None |
| ISP No. 6 | Soluble pigment | Slightly, Deep red | None |
| Waksman No. 1V | Growth | Fair, Deep red purple | Poor, Deep red purple |
| | Aerial mycelium | Moderate, Pale pink~pale yellowish pink | None |
| Waksman No. 7V | Soluble pigment | None | Vivid red purple |
| Utilization of carbon sources (using ISP No. 9) | Salicin | Positive | Negative |
| | D-Sorbitol (with B vitamins) | Positive | Negative |
| | Sucrose | Positive | Negative |
| | Inositol | Positive | Doubtful |
| | D-Mannitol | Positive | Doubtful |
| Hydrolysis of starch | | Positive (weak) | Negative |

The production of the antibiotic A, $A_1$, B or $B_1$ is by fermentation, i.e., by culturing on a medium the Strain that belongs to the genus Actinomadura and which produces the antibiotic FA-1180. The Strain can be cultured by a known method of cultivating actinomycetes or modifications thereof, for example, by submerged cultivation on a liquid medium. Any type of medium can be used if it contains a nutrient source utilizable by the Strain. Any known nutrient source that is employed in the ordinary cultivation of actinomycetes can be used. Illustrative carbon sources are carbohydrates such as glycerin, glucose, molasses and starch as well as fats such as animal fat, soybean oil, cotton seed oil and peanut oil. Illustrative nitrogen sources are urea, ammonium sulfate, nitrates, meat extract, yeast extract, corn steep liquor, peptone, casein, soybean meal, cotton seed meal and peanut meal. Illustrative inorganic salts are sodium chloride, phosphate salts, potassium chloride, calcium carbonate and magnesium sulfate. Various growth promoters and defoamers may be used depending on the need. Aerobic cultivation is preferred. The cultivation temperature is generally in the range of from 20° to 40° C., preferably from 25° to 35° C., the cultivation pH is generally from 4 to 9, preferably from 5 to 7, and the cultivation condition is aerobic. Under such cultivation conditions, the production of the antibiotic A, $A_1$, B or $B_1$ reaches a peak within a period of 7 to 20 days, preferably 10 to 15 days, whether tank cultivation or shake cultivation is performed.

The antibiotic A, $A_1$, B or $B_1$ can be recovered from the culture broth by a method commonly employed in the isolation of antibiotics from the culture broth of microorganisms. Generally, the antibiotic A, $A_1$, B and/or $B_1$ may be recovered from the culture filtrate and/or mycelial cake by extraction with water-immiscible organic solvents. Methods that suit the physicochemical properties of the particular antibiotic are selected based on the difference in solubility in solvents, the difference in crystallizability from the solution, the difference in affinity for adsorbents and the difference in distribution between liquid phases.

The antibiotics A, $A_1$, B or $B_1$ thus obtained has the physicochemical properties set forth below.

A. Properties of FA-1180 A (1) Color and nature: amphoteric dark red, needle-shaped crystal (2) Molecular weight: 659 (FD-Mass)

(3) Elemental analysis: Found: C 60.9%, H 6.2%, N 2.4%

(4) Melting point: 186° to 188° C. (with decomposition) (powder) 155° to 160° C. (with decomposition) (crystal)

Figure 7:
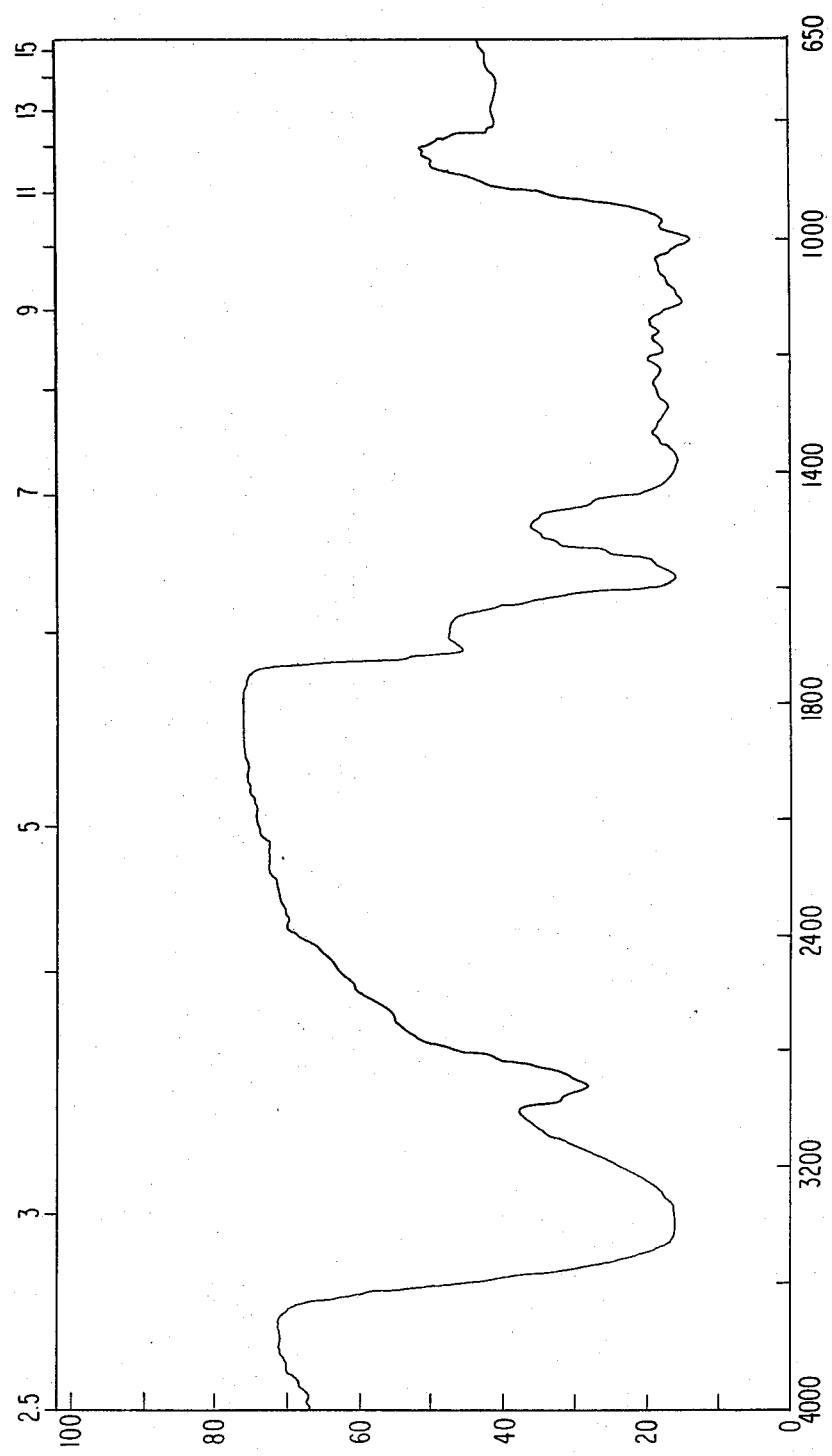
FIG. 7 is an IR spectrum of antibiotic FA-1180 A.
Figure 11:
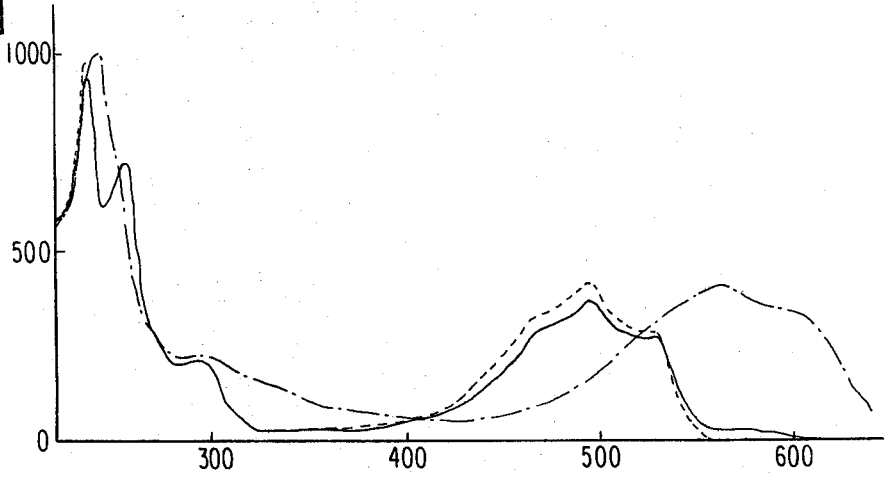
FIG. 11 is a UV and visible spectrum of antibiotic FA-1180 A.

(5) IR spectrum (determined by KBr method, see FIG. 7 which is an IR spectrum of antibiotic FA-1180 A as determined by KBr method): peaks at 3435-3310, 2920, 1708, 1586, 1388, 1292, 1230, 1198, 1168, 1110, 1008 and 968 $cm^{-1}$ (6) UV and visible spectrum (determined in methanol sol., see FIG. 11 which is a UV and visible spectrum of antibiotic FA-118 A, wherein the solid line is an absorption curve obtained in methanol solution, the broken line is obtained in 0.01 N hydrochloric acid/methanol solution, and the long and short dash line is in 0.01 N sodium hydroxide/methanol solution): 237 m$\mu$ ($E_{1\ cm}^{1\%}$ 980), 255 m$\mu$ ($E_{1\ cm}^{1\%}$ 760), 292 m$\mu$ ($E_{1\ cm}^{1\%}$ 230), 493 m$\mu$ ($E_{1\ cm}^{1\%}$ 390), 530 m$\mu$ ($E_{1\ cm}^{1\%}$ 270)

(7) TLC chromatography: TLC on silica gel with a developing solvent (chloroform:toluene:methanol=7:3:3); Rf=0.45

Figure 15:
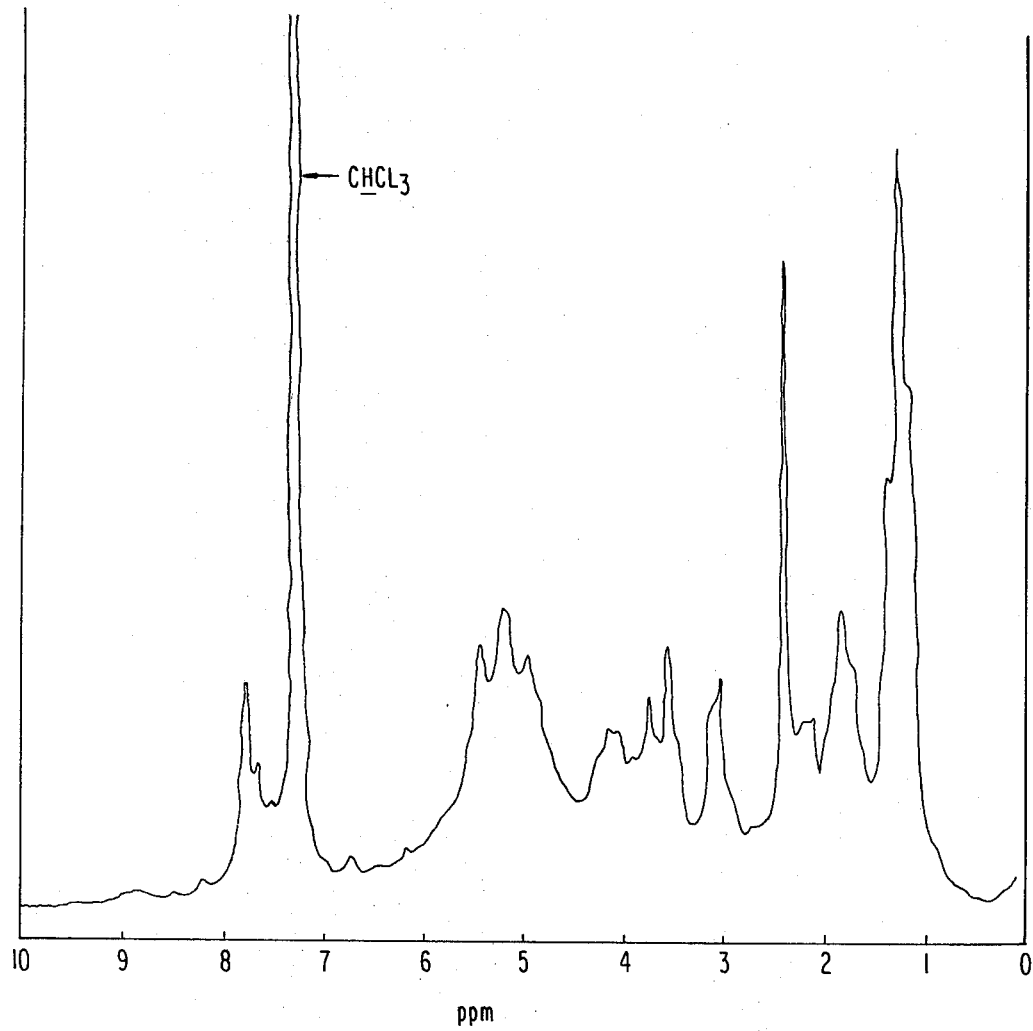
FIG. 15 is a PMR spectrum of antibiotic FA-1180 A.

(8) Solubility: freely soluble in methanol, soluble in chloroform, slightly soluble in n-hexane (9) PMR spectrum: see FIG. 15 which is a PMR spectrum of antibiotic FA-1180 A (60 MHz, in $CDCl_3$)

(10) Specific rotation: $[\alpha]_D^{24} + 147°$ (c=0.011, in $CHCl_3$)

B. Properties of FA-1180 $A_1$ (1) Color and nature: amphoteric dark red needle-shaped crystal (2) Elemental analysis: Found: C 58.7%, H 5.6%, N 1.9%

(3) Melting point: 175° to 185° C. (with decomposition) (powder)

Figure 8:
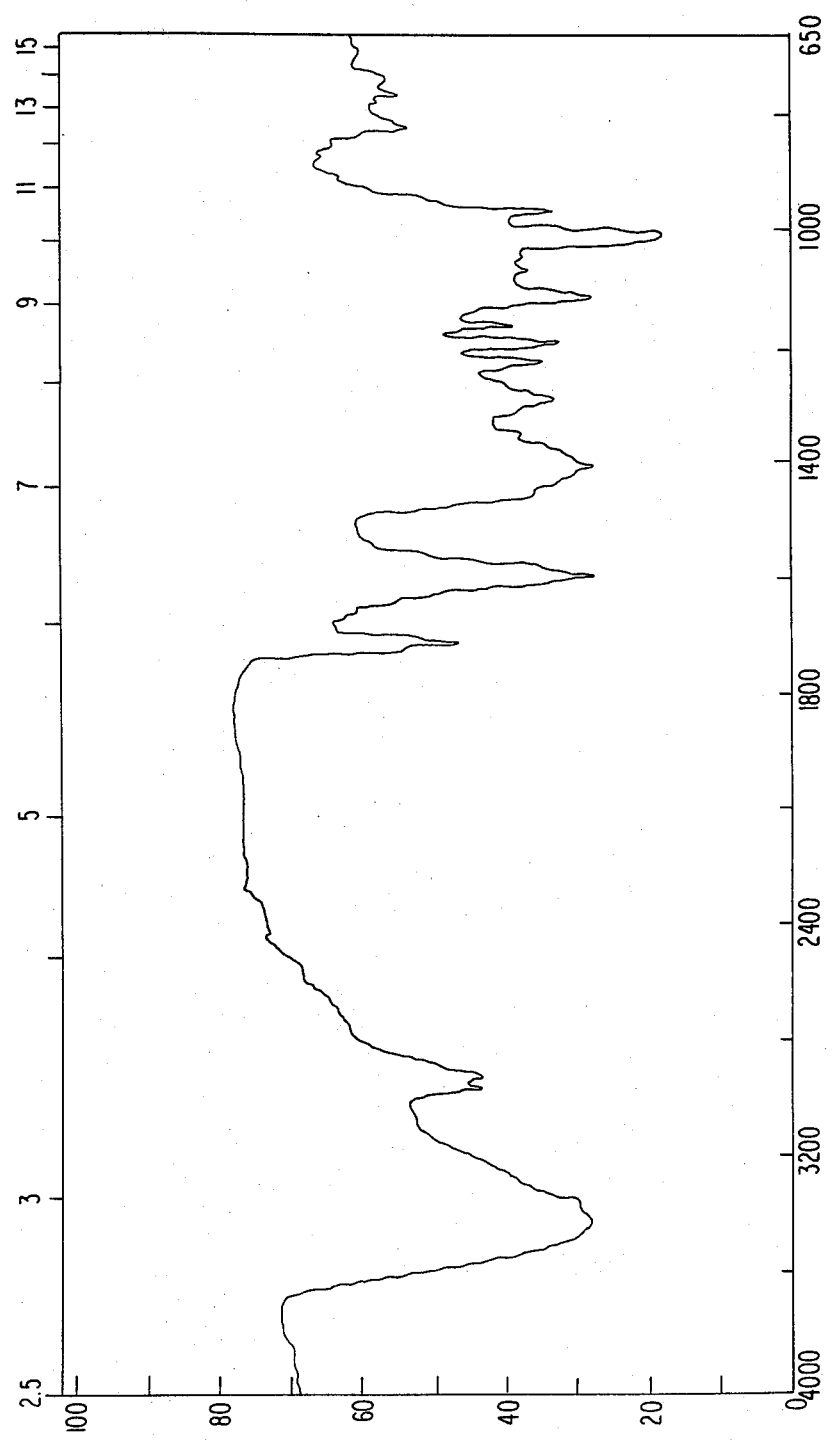
FIG. 8 is an IR spectrum of antibiotic FA-1180 $A_1$.
Figure 12:
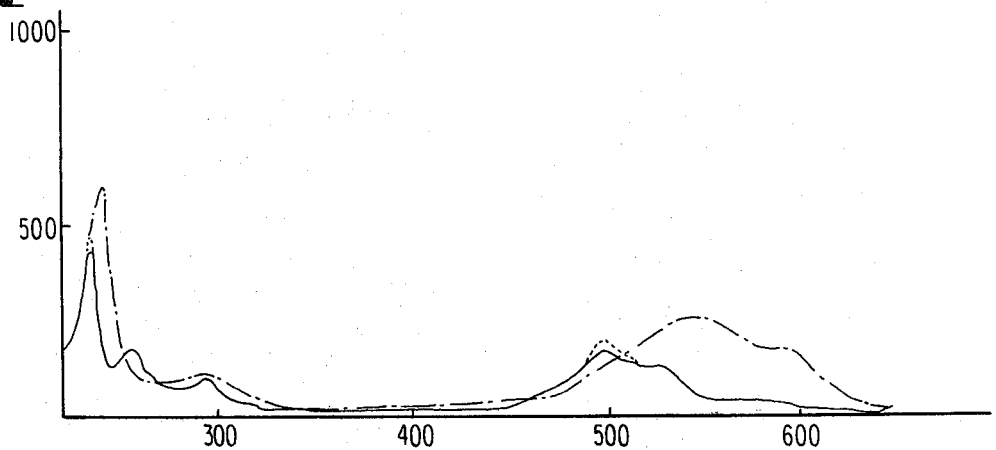
FIG. 12 is a UV and visible spectrum of antibiotic FA-1180 $A_1$.

(4) IR spectrum (see FIG. 8 which is an IR spectrum of antibiotic FA-1180 $A_1$ as determined by KBr method): peaks at 3435-3310, 2920, 1708, 1586, 1388, 1292, 1230, 1198, 1168, 1110, 1008 and 968 $cm^{-1}$ (5) UV and visible spectrum (determined in methanol sol., see FIG. 12 which is a UV and visible spectrum of antibiotic FA-1180 $A_1$, wherein the solid line is an absorption curve obtained in methanol solution, the broken line is obtained in 0.01 N hydrochloric acid/methanol solution, and the long and short dash line is in 0.01 N sodium hydroxide/methanol solution): 234 m$\mu$ ($E_{1\ cm}^{1\%}$ 457), 254 m$\mu$ ($E_{1\ cm}^{1\%}$ 351), 292 m$\mu$ ($E_{1\ cm}^{1\%}$ 101), 492 m$\mu$ ($E_{1\ cm}^{1\%}$ 172), 527 m$\mu$ ($E_{1\ cm}^{1\%}$ 132), 580 m$\mu$ ($E_{1\ cm}^{1\%}$ 30)

(6) TLC chromatography: TLC on silica gel with a developing solvent (chloroform:toluene:methanol=7:3:3); Rf=0.50

(7) Specific rotation: $[\alpha]_D^{24} + 185°$ (c=0.0085, in $CHCl_3$)

C. Properties of FA-1180 B (1) Color and nature: amphoteric dark red needle-shaped crystal (2) Elemental analysis: Found: C 59.9%, H 5.4%, N 2.3%

(3) Melting point: 198°-215° C. (with decomposition) (powder) 144°-146° C. (with decomposition) (crystal)

Figure 9:
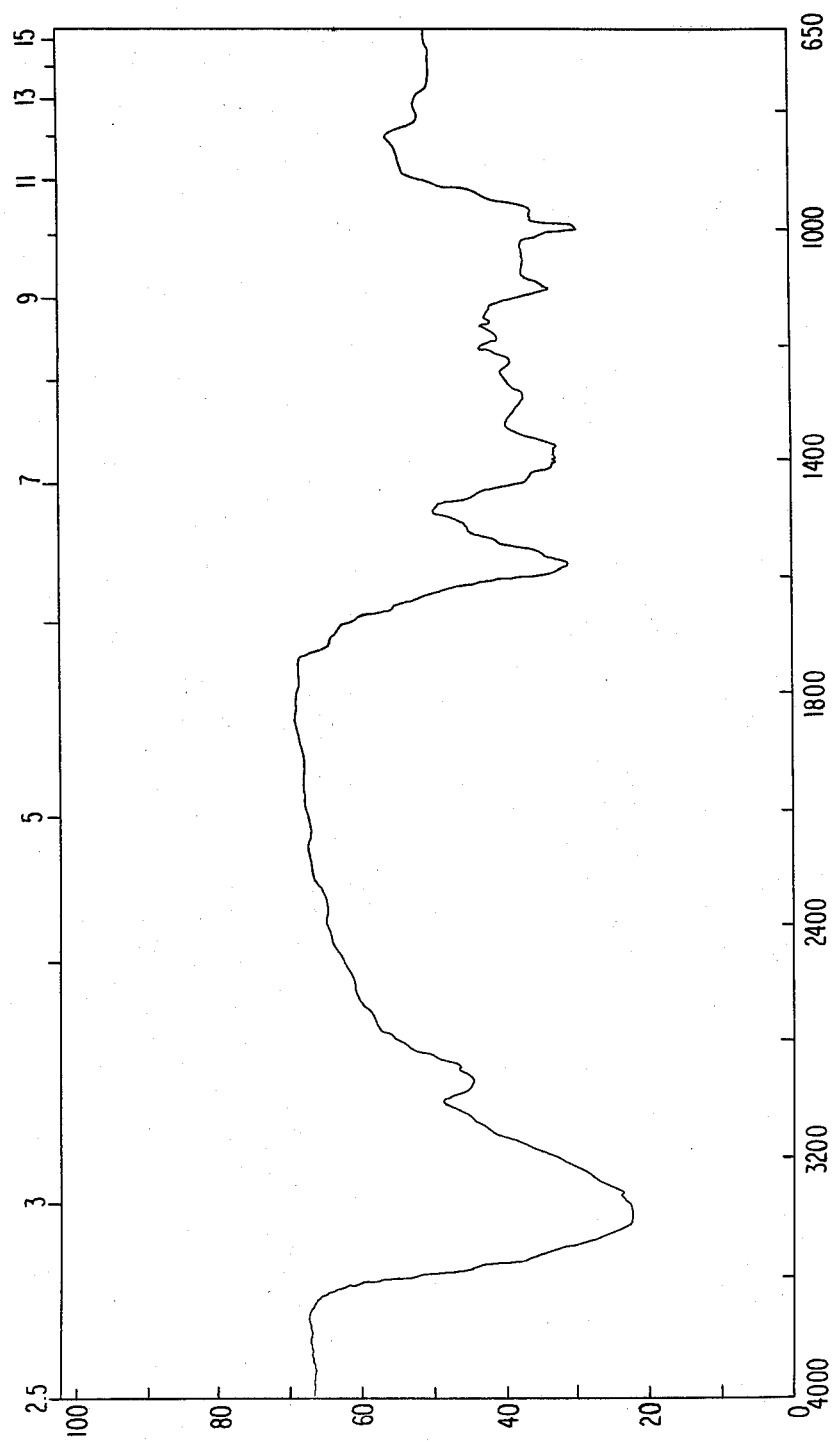
FIG. 9 is an IR spectrum of antibiotic FA-1180 B.
Figure 13:
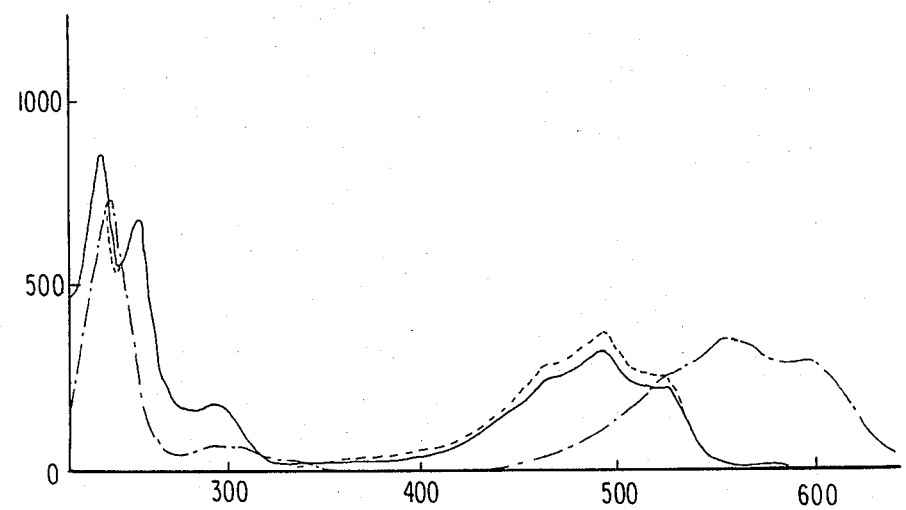
FIG. 13 is a UV and visible spectrum of antibiotic FA-1180 B.

(4) IR spectrum (determined by KBr method, see FIG. 9 which is an IR spectrum of antibiotic FA-1180 B as determined by KBr method): peaks at 3405, 2960, 1586, 1543, 1410, 1388, 1292, 1238, 1193, 1110, 1008 and 968 $cm^{-1}$ (5) UV and visible spectrum (determined in methanol sol., see FIG. 13 which is a UV and visible spectrum of antibiotic FA-1180 B, wherein the solid line is an absorption curve obtained in methanol solution, the broken line is obtained in 0.01 N hydrochloric acid/methanol solution, and the long and short dash line is in 0.01 N sodium hydroxide/methanol solution): 237 m$\mu$ ($E_{1\ cm}^{1\%}$ 850), 255 m$\mu$ ($E_{1\ cm}^{1\%}$ 660), 295 m$\mu$ ($E_{1\ cm}^{1\%}$ 200), 492 m$\mu$ ($E_{1\ cm}^{1\%}$ 350), 528 m$\mu$ ($E_{1\ cm}^{1\%}$ 250)

(6) TLC chromatography: TLC on silica gel with a developing solvent (chloroform:toluene:methanol=7:3:3); Rf=0.30

(7) Solubility: freely soluble in methanol, soluble in chloroform, slightly soluble in n-hexane (8) Specific rotation: unfixed $[\alpha]_D^{24} + 88° \sim -70°$ (c=0.01075, in methanol:chloroform=1:9)

D. Properties of FA-1180 $B_1$ (1) Color and nature: amphoteric dark red needle-shaped crystal (2) Elemental analysis: Found: C 58.4%, H 7.3%, N 19%

(3) Melting point: 152° to 154° C. (with decomposition) (crystal)

Figure 10:
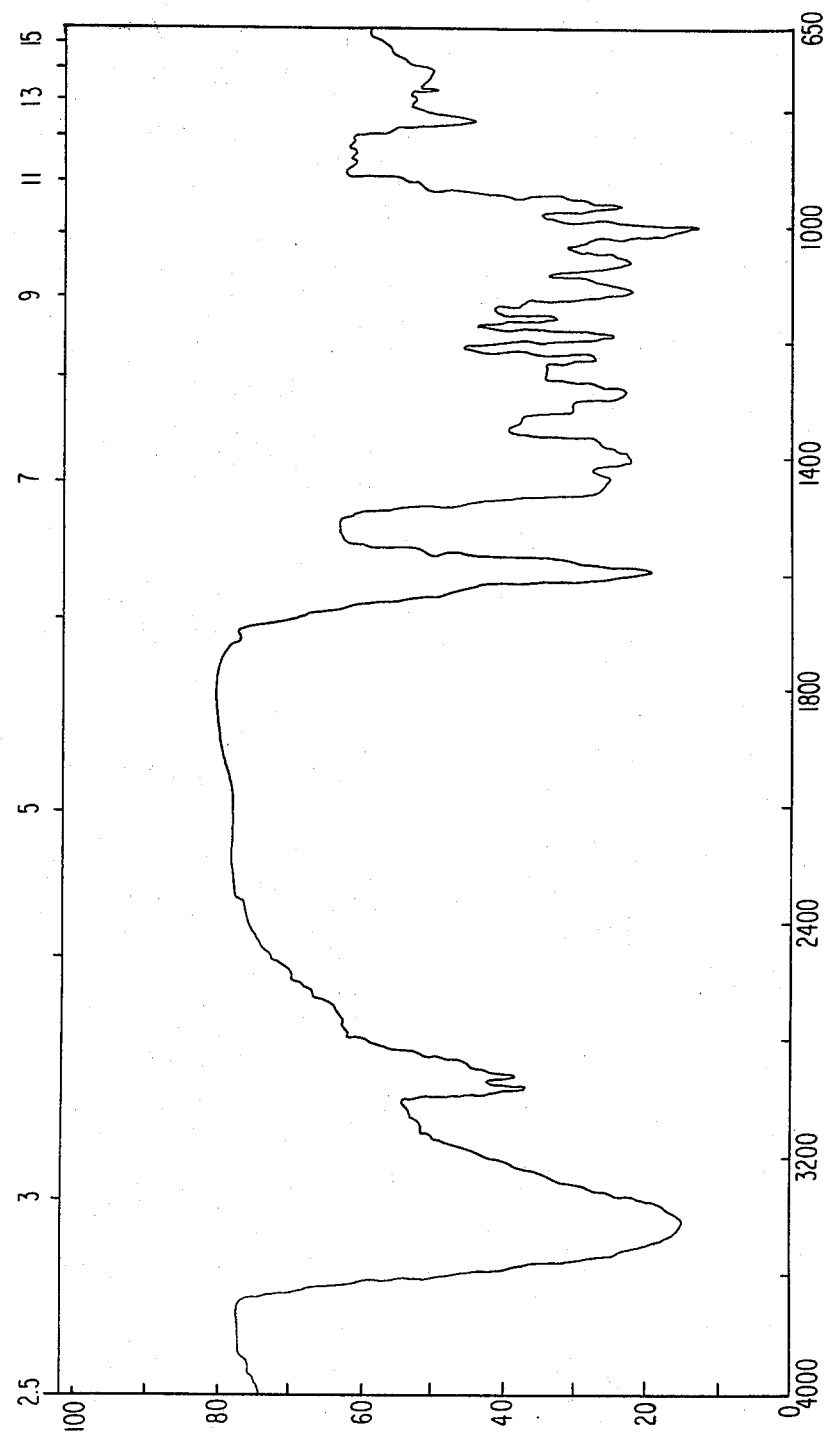
FIG. 10 is an IR spectrum of antibiotic FA-1180 $B_1$.
Figure 14:
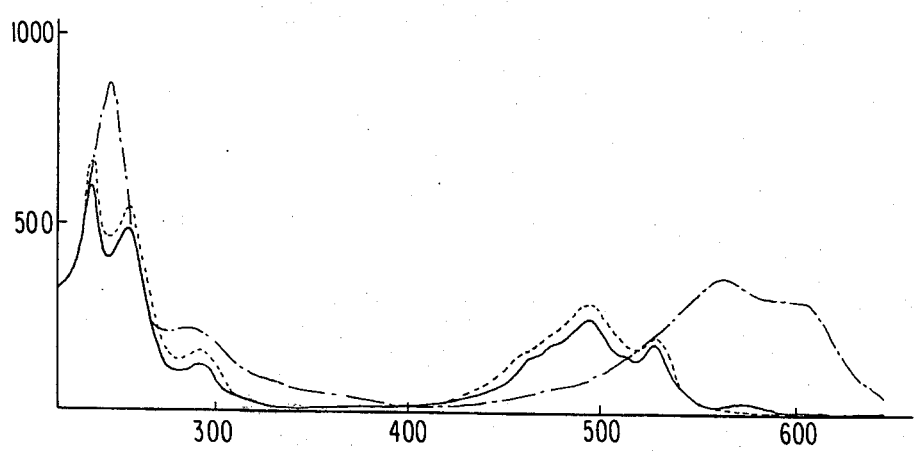
FIG. 14 is a UV and visible spectrum of antibiotic FA-1180 $B_1$.

(4) IR spectrum (see FIG. 10 which is an IR spectrum of antibiotic FA-1180 B₁ as determined by KBr method): peaks at 3420, 2960, 2920, 1600, 1420, 1300, 1230, 1200, 1160, 1120, 1060, 1010, 960 and 820 cm$^{-1}$ (5) UV and visible spectrum (determined in methanol sol., see FIG. 14 which is a UV and visible spectrum of antibiotic FA-1180 B₁, wherein the solid line is an absorption curve obtained in methanol solution, the broken line is obtained in 0.01 N hydrochloric acid/methanol solution, and the long and short dash line is in 0.01 N sodium hydroxide/methanol solution): 234 mμ ($E_{1\ cm}^{1\%}$ 603), 253 mμ ($E_{1\ cm}^{1\%}$ 487), 293 mμ ($E_{1\ cm}^{1\%}$ 133), 491 mμ ($E_{1\ cm}^{1\%}$ 249), 525 mμ ($E_{1\ cm}^{1\%}$ 186)

(6) TLC on silica gel with a developing solvent (chloroform:toluene:methanol=7:3:3); Rf=0.45

(7) Specific rotation: unfixed $[\alpha]_D^{24}$ +165° ~ +96° (c=0.013, in methanol:chloroform=1:9)

The present inventors supposed chemical structures of the present antibiotic A, A₁, B or B₁ from results of various measurements, consequently the present antibiotic is identified as anthracycline glycosides having the formula (I):

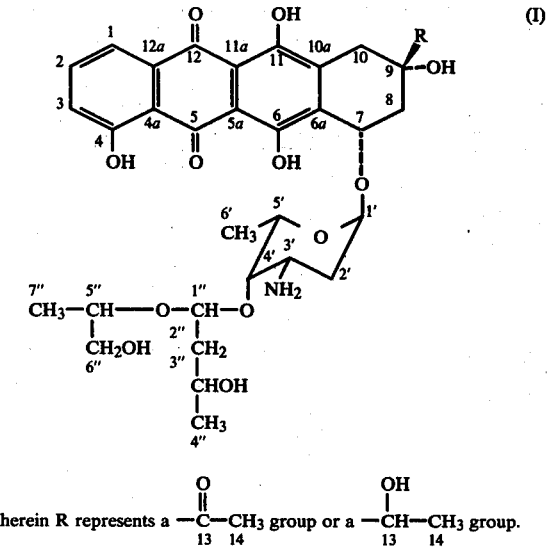

wherein R represents a $-\overset{O}{\underset{13}{\overset{\|}{C}}}-\overset{}{\underset{14}{CH_3}}$ group or a $-\overset{OH}{\underset{13}{\overset{|}{CH}}}-\overset{}{\underset{14}{CH_3}}$ group.

When R in the formula (I) represents an acetyl group, the present antibiotic is FA-1180 A or A₁. When R represents a 1-hydroxyethyl group, the present antibiotic is FA-1180 B or B₁. The present antibiotic A and A₁ or the present antibiotic B and B₁ are a stereoisomer, respectively. A carbon-13 nuclear magnetic resonance spectrum of the antibiotic was determined with an FX-60 Spectorometer (JEOL) operating at 15.04 MHz by dissolving about 30 mg of the antibiotic in 0.5 ml of CDCl₃ or in CD₃OD-CDCl₃ mixture and using tetramethylsilane (TMS) as the internal reference. Observed chemical shifts (in ppm relative to tetramethylsilane) and multiplicities for ¹³C magnetic resonance spectra of the antibiotic are as follows:

| | The Antibiotic ¹³CMR Listings | | | | | |
|---|---|---|---|---|---|---|
| No. | Assignments of Carbon* | Multiplicity | A(CDCl₃) | A₁(CDCl₃) | B (CDCl₃—CD₃OD) | B₁ (CDCl₃—CD₃OD) |
| 1 | 13 | s or d | 211.7 | 211.7 | 73.6 | 73.2 |
| 2 | 12 | s | 190.0 | 190.3 | 190.3 | 190.2 |
| 3 | 5 | s | 185.7 | 185.9 | 186.1 | 186.0 |
| 4 | 4 | s | 162.4 | 162.4 | 162.4 | 162.4 |
| 5 | 6 | s | 156.6 | 156.8 | 157.2 | 157.2 |
| 6 | 11 | s | 156.5 | 156.5 | 156.7 | 156.7 |
| 7 | 2 | d | 136.9 | 136.9 | 136.9 | 136.9 |
| 8 | 12a | s | 136.6 | 136.8 | 138.0 | 138.1 |
| 9 | 6a | s | 133.9 | 133.9 | 134.8 | 134.8 |
| 10 | 10a | s | 133.0 | 133.3 | 133.4 | 133.3 |
| 11 | 3 | d | 124.8 | 124.7 | 124.7 | 124.6 |
| 12 | 1 | d | 119.4 | 119.6 | 119.5 | 119.5 |
| 13 | 4a | s | 115.8 | 115.8 | 116.0 | 115.9 |
| 14 | 5a | s | 110.0 | 111.1 | 111.1 | 110.9 |
| 15 | 11a | s | 110.2 | 110.3 | 110.2 | 110.1 |
| 16 | 9 | s | 76.4 | 76.6 | 71.9 | 71.8 |
| 17 | 7 | d | 69.2 | 69.5 | 70.1 | 70.2 |
| 18 | 10 | t | 34.4 | 36.2 | 34.3 | 36.0 |
| 19 | 8 | t | 33.8 | 34.9 | 34.2 | 34.0 |
| 20 | 14 | q | 24.8 | 24.8 | (16.8) | (16.7) |
| 21 | 1' | d | 100.5 | 101.1 | 100.8 | 100.9 |
| 22 | 2' | t | 32.9 | 33.6 | 32.9 | 32.9 |
| 23 | 3' | d | 46.0 | 45.7 | 46.1 | 45.6 |
| 24 | 4' | d | 74.7 | 82.0 | 76.0 | 81.3 |
| 25 | 5' | d | 63.8 | 64.2 | 64.0 | 64.4 |

-continued

The Antibiotic $^{13}$CMR Listings

| No. | Assignments of Carbon* | Multi-plicity | A(CDCl$_3$) | A$_1$(CDCl$_3$) | B $\left(\begin{array}{c}\text{CDCl}_3-\\ \text{CD}_3\text{OD}\end{array}\right)$ | B$_1$ $\left(\begin{array}{c}\text{CDCl}_3-\\ \text{CD}_3\text{OD}\end{array}\right)$ |
|---|---|---|---|---|---|---|
| 26 | 6' | q | 16.3 | 17.0 | (16.6) | (16.7) |
| 27 | 1" | d | 101.0 | 106.7 | 101.7 | 106.2 |
| 28 | 2" | t | 42.3 | 45.4 | 42.9 | 45.8 |
| 29 | 3" | d | 72.7 | 75.8 | 73.3 | 75.9 |
| 30 | 4" | q | 23.7 | 23.3 | 23.4 | 23.1 |
| 31 | 5" | d | 67.5 | 67.9 | 67.8 | 67.8 |
| 32 | 6" | t | 66.2 | 66.8 | 66.5 | 66.5 |
| 33 | 7" | q | 17.3 | 18.1 | (17.4) | (18.0) |

*Note:
Assignments of carbon are shown in aforementioned formula (I).

The antibiotic A, A$_1$, B or B$_1$ is capable of reacting with a variety of acidic or basic substances to form the corresponding and pharmaceutically acceptable salts. A variety of acidic substances are an organic acid such as acetic acid, propionic acid, etc., a mineral acid such as hydrochloric acid, sulfuric acid, etc., and the others. A variety of basic substances are a hydroxide or carbonate of an alkali metal such as sodium, potassium, etc., and the others.

TEST EXAMPLE 1

The minimum inhibitory concentration (MIC) of the FA-1180 A, A$_1$, B or B$_1$ was determined by the agar dilution method, and the results are indicated in Table 5 below.

TABLE 5

| | MIC (ppm) | | | |
|---|---|---|---|---|
| Microorganisms | FA-1180 A | FA-1180 A$_1$ | FA-1180 B | FA-1180 B$_1$ |
| Bacillus subtilis PCI 219 | 1.56 | 1.56 | 6.25 | 3.125 |
| Bacillus subtilis 17 A | 1.56 | 1.56 | 12.5 | 12.5 |
| Bacillus subtilis 45 T | <0.2 | <0.2 | 0.4 | 0.4 |
| Bacillus cereus IAM 1729 | 3.125 | — | 25 | — |
| Staphylococcus aureus 209 P | 12.5 | 12.5 | 50 | 50 |
| Staphylococcus aureus | 12.5 | 12.5 | 50 | 50 |
| Escherichia coli NIHJ | >100 | >100 | >100 | >100 |
| Escherichia coli W3110 | >100 | >100 | >100 | >100 |
| Escherichia coli P3478 | >100 | >100 | >100 | >100 |
| Pseudomonas aeruginosa H | >100 | >100 | >100 | >100 |
| Salmonella typhimurium IFO 12529 | >100 | >100 | >100 | >100 |
| Klebsiella pneumoniae IFO 3512 | >100 | >100 | >100 | >100 |
| Serratia marcescens IFO 12648 | >100 | >100 | >100 | >100 |
| Candida albicans | >100 | >100 | >100 | >100 |

Notes:
(1) Medium: Brain heart infusion agar
(2) Determined: 18 hrs after inoculation

TEST EXAMPLE 2

Table 6 shows the results of a test for determining the therapeutic effect of the FA-1180 A, B and B$_1$ against P-388 Mice Leukemia. The test was conducted in accordance with the method described in *Cancer Chemotherapy Reports*, Part 3, Vol. 3, No. 2, p. 9, September 1972. Mice inoculated intraperitoneally with $1 \times 10^6$ cells of P-388 were administered with the test compounds daily on days 1 to 5. The activity (T/C) of the test compounds is represented by the ratio of the median survival time of the treated group to that of the control group.

TABLE 6

| Antibiotic | Dose (mg/kg/day) | Activity (T/C) (%) |
|---|---|---|
| FA-1180 A | 1.0 | 205 |
| | 0.5 | 167 |
| | 0.25 | 148 |
| FA-1180 B | 1.0 | 190 |
| | 0.5 | 162 |
| | 0.25 | 143 |
| FA-1180 B$_1$ | 1.0 | 179 |
| | 0.5 | 168 |
| | 0.25 | 151 |
| Control: 5-FU | 20 | 198 |

TEST EXAMPLE 3

The tumor cell suspension was prepared from cells taken from ascites of rats to which $1 \times 10^6$ cells of Yoshida rat sarcoma had been inoculated before 3 to 5 days. The ascites was diluted with a medium which was constituted from 80 to 90% (v/v) Fischer's solution containing 20 to 10% (v/v) desensitized horse serum. One half milliliter of the cell suspension containing $5 \sim 20 \times 10^4$ cells thus prepared was placed in a small test tube. A substance to be tested was dissolved and diluted with the same medium and 0.5 ml of the diluted solution was added to the cell suspension. To the control tube was added 0.5 ml of the medium. 2 to 5 tubes were used for each experimental units. They were incubated statically at 37° C. for 2 to 3 days. After the incubation, growth was measured by observing the quantity of precipitated cells on the bottom of the test tube with the naked eyes. Growth inhibitory effect of a substance was expressed by the concentration pointing 50 percent growth of the control growth.

TABLE 7

| Antibiotics | Growth Inhibitory Effect IC$_{50}$ (μg/ml) |
|---|---|
| Antibiotic FA-1180 A | $10^{-2}$ |
| Antibiotic FA-1180 A$_1$ | $10^{-3}$ |
| Antibiotic FA-1180 B | $10^{-2}$ |
| Antibiotic FA-1180 B$_1$ | $10^{-2}$ |
| Adriamycin hydrochloride | $10^{-2}$ |

IC$_{50}$: The concentration pointing 50% growth of the control growth.

The antibiotics A, A$_1$, B and B$_1$ are classified as anthracycline glycosides, but the antibiotics of this invention had novel chemical structure and none of the documented anthracycline glycosides had the same physicochemical properties as those of the antibiotics of this invention. Therefore, we concluded that the antibiotics FA-1180 A, $A_1$, B and $B_1$ and salts thereof are novel substances.

The antibiotics A, $A_1$, B and $B_1$ and salts thereof have a strong ability to inhibit the growth of Gram-positive bacteria and they also have antitumor activity, so they are useful as an active ingredient for medicines such as disinfectants for medical devices or chemotherapeutics against microorganisms in human beings and animals. Especially the antibiotic B is useful as an active ingredient for medicines. The antibiotics of this invention are formulated and used in a manner analogous to that for ordinary antibiotics for medical applications. For example, the antibiotics of the invention and an inert diluent are formulated in a powder, tablet, lozenge, capsule, suspension, syrup, cream, ointment or injection, and used. Usually, these antibiotics are administered at a dosage of 0.1 to 20 mg/kg/day.

This invention is now described in greater detail by reference to the following example which is given here for illustrative purposes only and is by no means intended to limit the scope of the invention.

EXAMPLE (1) Fermentation

One liter of a broth containing 20 g of glucose, 10 g of corn steep liquor, 10 g of soybean meal, 2 g of potassium nitrate, 5 g of sodium chloride and 0.5 g of magnesium sulfate and which was adjusted to a pH of 7.0 was prepared. Fifteen milliliters of the broth was placed in a 50 ml test tube. The tube was sterilized by the conventional method. The broth in the test tube was inoculated with spores of the strain FA-1180 which were subjected to a shaking cultivation at 30° C. for 10 days to produce a first seed. A second seed was prepared in a similar manner by shaking cultivation at 30°–35° C. in a 2-liter flask containing 350 ml of the remaining broth. Then, a 50-liter jar fermentor was charged with 35 liters of a broth having the same composition as specified above, and after sterilization, the broth was inoculated with 700 ml of the second seed which was cultured at 28°–30° C. for 14 days with air supplied at a rate of 35 liters per minute and the agitator rotated at 250 rpm.

(2) Extraction

After the fermentation, 70 liters of the liquid culture was separated into the mycelial cake and filtrate by filtration. The cake was extracted three times with 3-liter portions of acetone, followed by concentration under vacuum. The concentrate was extracted twice each with a mixture comprising 300 ml of water, 200 ml of a saturated aqueous solution of sodium bicarbonate and one liter of chloroform. After concentrating the chloroform layer in vacuum, the concentrate was extracted three times with 500 ml portions of aqueous solution of 0.01 N acetic acid. The resulting orange extract was neutralized with an aqueous solution of 2 N sodium hydroxide until it turned dark red, and the extract was again extracted with one liter of chloroform. The extract was then concentrated in vacuum, mixed with a great excess of n-hexane to form a precipitate which was filtered off and dried to give about 200 mg of a dark red crude powder.

(3) Purification (3-1) A solution of 200 mg of the crude powder in a small amount of methanol was applied to twenty silica gel sheets for TLC chromatography (Art. 5553 of Merck & Co., Inc.) and developed to 15 cm from the placing point with a solvent comprising chloroform:toluene:methanol=7:3:3. After the development, red spots having Rf values of 0.45 and 0.3 were collected and extracted with methanol. The respective extracts soluble in chloroform were concentrated to give 28 mg of FA-1180 A and 7 mg of FA-1180 B.

(3-2) Further purification of the complex (160 mg) into its components was achieved by droplet counter-current chromatography (DCC) with chloroform:methanol:0.1 N acetic acid=5:5:3 as solvent system. DCC apparatus contained 300 separation tubes was used and separation was accomplished by down flow method. The effluent was monitored by TLC on silica gel plate with a solvent system of chloroform:toluene:methanol (7:3:3) or lower phase of chloroform:methanol:0.1 N acetic acid (5:5:3).

The fractions containing each components were pooled separately and adjusted to pH 8.6 with sodium bicarbonate saturated solution. In this treatment, the each fraction was separated into a solvent layer and an aqueous layer. Separated solvent layer washed with deionized water and dried with anhydrous sodium sulfate, concentrated in vacuo to small volume, and then crystallized from chloroform-n-hexane for FA-1180 A (40 mg) and FA-1180 $A_1$ (8 mg) or chloroform for FA-1180 B (7 mg) and FA-1180 $B_1$ (7 mg).

While the invention has been described in detail and with reference to specific embodiments thereof, it will be apparent to one skilled in the art that various changes and modifications can be made therein without departing from the spirit and scope thereof.

What is claimed is:

1. An anthracycline antibiotic selected from the group consisting of FA-1180 B and FA-1180 $B_1$, or a pharmaceutically acceptable salt thereof, said antibiotic having the formula (I):

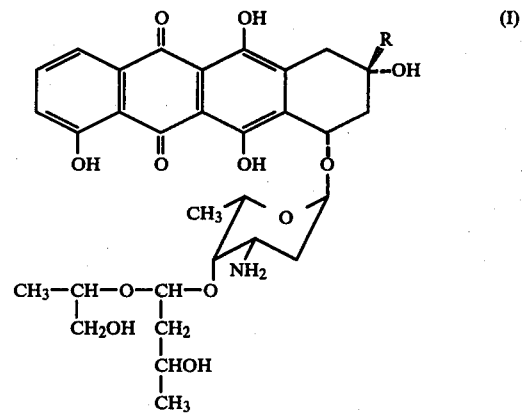

wherein R represents a 1-hydroxyethyl group.

* * * * *